United States Patent
Koverech

(10) Patent No.: US 8,394,854 B2
(45) Date of Patent: Mar. 12, 2013

(54) USE OF L-CARNITINE FOR THE TREATMENT OF CARDIOVASCULAR DISEASES

(75) Inventor: Aleardo Koverech, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 212 days.

(21) Appl. No.: 12/972,617

(22) Filed: Dec. 20, 2010

(65) Prior Publication Data

US 2011/0086917 A1   Apr. 14, 2011

Related U.S. Application Data

(63) Continuation of application No. 11/629,202, filed as application No. PCT/EP2005/006657 on Jun. 21, 2005, now Pat. No. 7,879,908.

(30) Foreign Application Priority Data

Jul. 13, 2004  (IT) .............................. RM2004A0346

(51) Int. Cl.
*A61K 31/205*   (2006.01)
*A61P 9/10*   (2006.01)

(52) U.S. Cl. ........................... 514/556; 514/23; 514/546

(58) Field of Classification Search ................... 514/556
See application file for complete search history.

(56) References Cited

U.S. PATENT DOCUMENTS

| 4,320,145 | A | 3/1982 | Cavazza et al. |
| 6,221,851 | B1 | 4/2001 | Feldman |
| 2002/0002202 | A1 | 1/2002 | Cavazza et al. |

FOREIGN PATENT DOCUMENTS

| EP | 0 627 161 | | 12/1994 |
| JP | 115220 | A3 | 8/1990 |
| WO | 01/26649 | | 4/2001 |
| WO | 03/082800 | A1 | 10/2003 |
| WO | 2004/091602 | | 10/2004 |

OTHER PUBLICATIONS

Junyou, C. et al. "Observation of Effect of Clinic Treatment of AMI Using L-carnitine in Early Stages" Jiangsu Journal of Clinical Medicine, vol. 3, No. 4, pp. 331-332, Dec. 31, 1999.

Walker, "Role of Vital Statistics in Medical Science" read before the Vital Statistic Section of the American Public Health Association as the Sixty-fifth Annual Meeting in New Orleans, LA, Oct. 20, 1936.
Pfeffer et al., Circulation, 1990; 81; 1161-1172.
Iliceto et al., "Effects of L-Carnitine Administration on Left Ventricular Remodeling After Acute Anterior Myocardial Infarction: The CEDIM trial" J. of American College of Cardiology 1995: 26(2);380-387.
International Search Report for PCT/EP2005/006657 mailed Apr. 7, 2006.
Arsenian et al., "Safety, tolerability and efficacy of a glucose-insulin-potassium-magnesium-carnitine solution in acute myocardial infarction" American Journal of Cardiology, vol. 78, No. 4, 1996, pp. 476-479.
Grandi et al., "Effect of acute carnitine administration on glucose insulin metabolism in healthy subjects" International Journal of Clinical Pharmacology Research, vol. 17, No. 4, 1997, pp. 143-147.
Iliceto, Sabino, et al., "Effects of L-Carnitine Administration on Left Ventricular Remodeling After Acute Anterior Myocardial Infraction: The L-Carnitine Ecocardiografia Digitalizzata Infarto Miocardico (CEDIM) Trial", Journal of the American College of Cardiology, vol. 26, No. 2, 1995, pp. 380-387.
Singh, RB, et al., "A randomised, double-blind, placebo-controlled trial of L-carnitine in suspected acute myocardial infarction", Postgrad. Med. J; 1996; vol. 72, pp. 45-50.

*Primary Examiner* — Walter Webb

(74) *Attorney, Agent, or Firm* — Lucas & Mercanti, LLP

(57) ABSTRACT

The use of L-carnitine, or one of its pharmaceutically acceptable salts, is described in combination with glucose for the preparation of a medicament useful for diminishing the number of deaths caused by acute myocardial infarction, for reducing the number of days infarction patients spend in intensive care in hospital, and for reducing the number of episodes of post-infarction heart failure, in which the L-carnitine is administered intravenously within only a few hours of the onset of symptoms of acute myocardial infarction at an initial dose of 9 grams a day in combination with 1000-1500 mL of a 5% glucose solution for 5 days, after which the L-carnitine treatment is continued at a dose of 4 grams a day administered orally.

6 Claims, No Drawings

USE OF L-CARNITINE FOR THE TREATMENT OF CARDIOVASCULAR DISEASES

This application is a continuation of U.S. application Ser. No. 11/629,202 filed on Jan. 8, 2007 which is a 371 U.S. national phase of International Application No. PCT/EP05/06657 filed on Jun. 21, 2005, which claims priority to and benefit of Italian Application No. RM2004A000346 filed on Jul. 13, 2004, all of which are incorporated by reference herein in their entirety.

The present invention relates to the combined use of L-carnitine and glucose as a medicament useful for diminishing the number of deaths caused by acute myocardial infarction, for reducing the number of days infarction patients spend in intensive care in hospital, and for reducing the number of episodes of post-infarction heart failure.

The daily dose of L-carnitine to be administered must be dissolved in two or three 500 ml vials of 5% glucose solution and administered intravenously. It is important that the treatment with the combination according to the invention should begin within only a few hours of the onset of acute myocardial infarction symptoms, at an initial dose of 9 grams a day for 5 days, after which the treatment should be continued at a dose of 4 grams a day with L-carnitine alone, administered orally.

Post-infarction heart failure is due to inability of the heart to pump blood in sufficient amounts to meet the metabolic needs of the various tissues.

Acute myocardial infarction (AMI) causes morphofunctional alterations which often induce progressive left ventricular dilatation ("ventricular remodelling" phenomenon).

Post-AMI ventricular dilatation may be regarded as a global compensation mechanism aimed at maintaining an adequate cardiac output in the presence of a reduction in ejection fraction.

The extent of the ventricular dilatation is the most important prognostic indicator in patients with AMI.

Patients with relatively larger ventricular volumes are at greater risk of future cardiac events (Circulation 1987; 76:44-51).

Limitation of the post-infarction ventricular remodelling phenomenon is therefore of major importance from the clinico-prognostic point of view (Circulation 1994; 89:68-75). Limitation of this phenomenon can be achieved by two mechanisms: (a) by limiting the extent of the infarcted area (which is the main determinant of future dilatation) by means of early myocardial reperfusion (Circulation 1989; 79:441-444) and/or (b) by reducing the parietal stress and consequently the progressive dilatation of the area of the myocardium not involved in the infarction process by means of the administration of ACE inhibitors.

When the thrombotic obstruction evolves rapidly in the direction of total, permanent vascular occlusion, the resulting lack of perfusion gives rise, in the space of only a few hours, to myocardial cellular necrosis and thus to infarction. The immediate and longer-term prognosis will depend on a series of factors, the most important of which being the size of the necrotic area and the early and late complications resulting from it. It is therefore obvious that the primary aim of modern acute infarction therapy is to reduce the size of the infarcted area. This aim is often achieved by means of reperfusion procedures, whether pharmacological (thrombolytic), mechanical (PTCA) such as angioplasty, or surgical (bypass). Generally speaking, the earlier and more effective the reperfusion, the smaller will be the necrotic area. The latter is also influenced, albeit to a lesser extent, by other factors, the first of which is myocardial oxygen consumption, which is conditioned by heart rate, myocardial contractility and parietal tension. Of fundamental importance then will be all those measures, whether pharmacological or otherwise, that reduce the cardiac workload, while at the same time maintaining adequate circulatory output.

Of all subjects who die as a result of acute myocardial infarction, more than half do so within the first few hours.

Drugs useful for the treatment of heart failure and acute myocardial infarction are already known.

Beta-blockers are drugs endowed with antiarrhythmia properties and are significantly more active if used in the early phases of onset of infarction.

Nitroderivatives are drugs usually administered by venous infusion, and are useful for improving myocardial perfusion through vasodilatation of the epicardial vessels.

Sodium nitroprusside is a drug that exerts a dual action on the arteriolar and venous districts. This compound produces coronary and renal vasodilatation, thus enhancing myocardial perfusion and diuresis.

L-carnitine is a known compound, whose preparation process is described in U.S. Pat. No. 4,254,053.

The use of L-carnitine in combination with glucose is already known.

U.S. Pat. No. 4,320,145 describes a glucose solution containing L-carnitine which is useful for favouring the muscular absorption of the glucose and thus for preventing excessive insulin secretion.

The use of L-carnitine for the treatment of heart diseases is also known.

In Drugs Exp. Clin. Res 1992; 18(8):355-65 the use of L-carnitine is described in infarction patients, in whom oral treatment with L-carnitine was initiated after the patients had been discharged from hospital.

In Eur Heart J. 1989 June; 10(6):502-8 the use of L-carnitine is described in infarction patients, in whom the antiarrhythmia and metabolic effects of L-carnitine are evaluated. In this study, it is reported that there were two deaths each in the group treated with L-carnitine and in that treated with placebo.

In J. Am. Coll. Cardiol 1995 August; 26(2):380-7 the prolonged use of L-carnitine in infarction patients is described, and its effect on left ventricular volume at 3, 6 and 12 months after the start of treatment. In this study, L-carnitine was administered within 24 hours of the infarction and the mortality assessment showed that 11 patients in the treated group died over the entire hospitalisation period as against 14 in the control group. The non-significance of the difference in the number of deaths observed in the two groups tested is evident.

In Am. Heart J. 2000 February; 139(2 Pt 3):S115-9, which is a review of the metabolic effects of L-carnitine in the cardiological field, it is reported that L-carnitine is effective because it has metabolic effects on lipid and carbohydrate metabolism.

In Lancet 1982 Jun. 19; 1(8286):1419-20 it is reported that analyses of heart tissue samples of patients dying of infarction, in parallel with heart tissue samples from people dying due to causes other than infarct, show that in the cardiac areas not affected by infarction (of cardiopathic patients) the level of free carnitine was equal to that of controls, whereas the level of free carnitine in the area of infarcted heart tissue was lower than that in controls.

In Postgrad Med. J. 1996 January; 72(843):45-50 the use of L-carnitine is described in patients presenting infarction symptoms in the 24-hour period prior to the start of treatment. In this study, L-carnitine was administered at a dose of 2 g/day, and the number of deaths at 28 days after the start of treatment was 6 in the control group and 4 in the treated group. The non-significance of the difference in the number of deaths observed in the two groups tested is evident.

In Am. J. Cardiovasc Pathol 1990; 3(2):131-42 the use of L-carnitine is described in an experimental cardiac ischaemia model in experimental animals (dogs) where L-carnitine proved active in enhancing cardiac lipid metabolism in these animals.

In Drugs Exptl. Clin. Res. X(4) 219-223 (1984) the use of L-carnitine at a dose of 40 mg/kg/day (2.8 g/day) is described. The number of deaths in the control group was one, as against none in the treated group. Moreover, in this study the treated group was divided into two subgroups one of which was treated with L-carnitine within 4 hours of onset of signs of infarction and the other treated 4 hours after the onset of signs of infarction. In their discussion of the results the authors state that they found no statistically significant difference between patients treated within 4 hours of onset of symptoms of infarction and patients treated 4 hours after the onset of such symptoms.

In a further publication entitled "Clinical aspects of human carnitine deficiency" published by "Pergamon Press 1986" a "blind" clinical trial is described in which 351 patients with acute myocardial infarction were recruited whose infarction symptoms had set in within 8 hours of the start of treatment with L-carnitine. In this clinical trial the patients received 3 grams of L-carnitine every 8 hours (9 grams a day) intravenously. The L-carnitine treatment was continued for 48 hours (the control group received saline solution). Analysis of the mortality at 7 days after the start of treatment showed no significant difference between the control groups and the group treated with L-carnitine.

In none of these studies with L-carnitine (or other studies not mentioned in the present application) is it claimed or suggested that L-carnitine in combination with glucose is useful for the treatment of post-infarction heart failure, for reducing the number of days infarction patients spend in intensive care in hospital, and for reducing the number of deaths caused by acute myocardial infarction.

A certain number of patients with acute myocardial infarction still continue to die during the first week of hospitalisation in intensive care departments, and also later, even when treated with all the appropriate pharmacological and technical means available. Furthermore, L-carnitine alone, whether using the therapeutic regimens adopted to date and described in the above-cited publications, or in combination with said appropriate and available pharmacological and technical means, though improving the general condition of the patients treated, fails to reduce the mortality compared to patients treated with the normal drugs used.

There is therefore still a strongly perceived need for new drugs or new combinations useful for diminishing the number of deaths caused by acute myocardial infarction, for reducing the number of days infarction patients spend in intensive care in hospital, and for reducing the number of episodes of post-infarction heart failure.

It has now surprisingly and unexpectedly been found that the combined use of L-carnitine or one of its pharmaceutically acceptable salts together with glucose is useful for diminishing the number of deaths caused by acute myocardial infarction, for reducing the number of days infarction patients spend in intensive care in hospital, and for reducing the number of episodes of post-infarction heart failure.

What is meant by the combined use of L-carnitine and glucose is the simultaneous administration of a 5% glucose solution (1000/1500 mL/day i.v.) in which 9 grams of L-carnitine are dissolved, or the administration of 5% glucose solution (1000/1500 mL/day i.v.) and the parallel administration of 9 grams/day i.v. of L-carnitine in a single dose or in divided doses (e.g. 3 g×3 administrations/day i.v).

What is meant by pharmaceutically acceptable salt of L-carnitine is any salt of the latter with an acid that gives rise to no toxic or side effects.

These acids are well known to pharmacologists and to experts in pharmacy; non-limiting examples of such salts are: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino ethanesulphonate, magnesium 2-amino ethanesulphonate, methanesulphonate, choline tartrate, trichloroacetate, and trifluoroacetate.

What is meant by pharmaceutically acceptable salt of L-carnitine is also a salt approved by the FDA and listed in the publication Int. J. of Pharm. 33 (1986), 201-217, incorporated herein as a reference.

The object of the present invention then is the combined use of L-carnitine or one of its pharmaceutically acceptable salts in combination with glucose, in which the intravenous treatment with L-carnitine and glucose is initiated within only a few hours of onset of the symptoms of acute myocardial infarction, preferably within 6 hours, and more preferably within 4 hours of the onset of acute myocardial infarction symptoms; the treatment is administered for 5 days consecutively at an initial L-carnitine dose of 9 grams a day dissolved in 1000-1500 mL of 5% glucose solution, after which the L-carnitine treatment is continued orally at a dose of 4 grams a day; for the preparation of a medicament useful for diminishing the number of deaths caused by acute myocardial infarction, for reducing the number of days infarction patients spend in intensive care in hospital, and for reducing the number of episodes of post-infarction heart failure.

The following example illustrates the invention.

EXAMPLE 1

A clinical trial was conducted aimed at evaluating the effect of the administration of L-carnitine on short-, medium- and long-term incidence and mortality in patients with acute myocardial infarction. The trial design was that of a multi-centre randomized, double-blind, placebo-controlled, parallel-group trial.

A total of 2,296 patients of male and female sex were recruited, aged below 80 years, subdivided into groups. The study compound, L-carnitine, was administered at a dose of 9 g/day i.v. for the first 5 days and 4 g/day by mouth from day 6 to day 180.

In particular, in one group of patients the L-carnitine was administered intravenously dissolved in sterile saline solution, while in another group of patients it was administered dissolved in normal 5% glucose solution used in hospital departments.

The control group received the standard therapy used for the treatment of infarct, without L-carnitine.

Concomitant therapies were administered according to the procedures adopted in local clinical practice.

The efficacy parameters evaluated were reduction of mortality, reduction of the number of days spent in intensive care, and reduction of the number of episodes of post-infarction heart failure.

Inclusion Criteria

Typical chest pain lasting >30 minutes which is not relieved by oral or i.v. administration of nitrates;

ECG with ST-segment elevation 0.2 mV in D, and in lead aVL and/or in at least two contiguous precordial leads;
Time interval elapsing between onset of symptoms and study randomisation <12 hours;
Age <80 years;
Written informed consent.

Exclusion Criteria
Pregnancy or breast-feeding;
Haemodynamically significant valvulopathy;
Hypertrophic or dilatory cardiomyopathy;
Congenital cardiopathy;
Clinically severe liver and kidney disease;
Alcohol abuse;
Other diseases associated with a poor life expectancy;
Conditions making poor compliance with treatment and/or periodic examinations likely;
Inclusion in another trial.

The patients treated with 9 g/day of L-carnitine dissolved in 1000/1500 mL of glucose solution showed a lower mortality rate than the control group, and said mortality was comparable to that recorded in the group treated with L-carnitine dissolved in saline. For this reason, Table 1/A here below gives the mortality data in the placebo group compared to patients treated with L-carnitine, regardless of whether the L-carnitine was dissolved in saline or in glucose solution (totality of patients included in the trial).

TABLE 1/A

| | NUMBER OF DEATHS AT: | | | | | | |
|---|---|---|---|---|---|---|---|
| | 3 days | 5 days | 7 days | 1 mo. | 2 mos. | 6 mos. | 12 mos. |
| Placebo | 34 | 43 | 45 | 58 | 65 | 74 | 75 |
| L-carnitine | 23 | 27 | 31 | 45 | 53 | 64 | 67 |
| RR | 0.68 | 0.63 | 0.69 | 0.78 | 0.81 | 0.86 | 0.89 |
| P | 0.1357 | 0.0498 | 0.097 | 0.1766 | 0.238 | 0.3546 | 0.4555 |

RR = Relative Risk.

Table 1/B here below gives the mortality data in the patient group treated with L-carnitine dissolved in glucose solution compared to the control group treated with placebo.

TABLE 1/B

| | NUMBER OF DEATHS AT: | | | | | | |
|---|---|---|---|---|---|---|---|
| | 3 days | 5 days | 7 days | 1 mo. | 2 mos. | 6 mos. | 12 mos. |
| Placebo | 17 | 21 | 22 | 29 | 33 | 37 | 38 |
| L-carnitine | 11 | 13 | 15 | 22 | 26 | 32 | 33 |
| RR | 0.67 | 0.64 | 0.70 | 0.79 | 0.80 | 0.87 | 0.88 |
| P | 0.1356 | 0.0497 | 0.099 | 0.1768 | 0.237 | 0.3548 | 0.4553 |

RR = Relative Risk.

The group of infarction patients treated with L-carnitine dissolved in glucose solution presented a statistically significant reduction in the number of days in intensive care compared to the group of patients treated with L-carnitine dissolved in saline. The results obtained are reported in Table 2.

TABLE 2

LENGTH OF STAY IN INTENSIVE CARE UNIT

| L-carnitine in saline | 6 days |
|---|---|
| L-carnitine and glucose | 5 days |

TABLE 2-continued

LENGTH OF STAY IN INTENSIVE CARE UNIT

| solution | |
|---|---|
| Significance | $P \leq 0.05$ |

The group of patients treated with L-carnitine and glucose solution showed a statistically significant reduction in the number of episodes of post-infarction heart failure compared to the patient group treated with L-carnitine dissolved in saline.

The results obtained are reported in Table 3.

TABLE 3

EPISODES OF POST-INFARCTION HEART FAILURE

| L-carnitine in saline | n = 16 |
|---|---|
| L-carnitine and glucose solution | n = 9 |
| Significance | $P \leq 0.001$ |

The L-carnitine doses used according to the present invention and the treatment regimen may be subject to changes, as advised by the primary care physician on the basis of his or her experience and the patient's general condition, also thanks to the lack of toxicity of the compound according to the invention.

The intravenous administration formulations, according to the present invention, include solutions or suspensions in suitable vehicles such as, for example, saline solution, distilled water, glucose solution, or others.

The oral administration formulations, according to the present invention, include tablets, capsules, powders, granules, syrups, elixirs, solutions or suspensions.

The invention claimed is:
1. A method for reducing the number of episodes of death caused by acute myocardial infarction in patients as compared to a control group treated with L-carnitine in saline comprising intravenously administering L-carnitine or one of its pharmaceutically acceptable salts within 6 hours of the onset of symptoms of acute myocardial infarction to patients in need thereof, at an initial dose of 9 grams a day, in combination with 1000-1500 ml of a 5% glucose solution for 5 days, followed by orally administering the L-carnitine or one of its pharmaceutically acceptable salts at a dose of 4 grams a day, whereby said number of episodes of death caused by acute myocardial infarction are reduced compared to said control group.

2. The method according to claim 1, in which the L-carnitine and the glucose solution are administered within 4 hours of the onset of symptoms of acute myocardial infarction.

3. The method according to claim 1, in which the pharmaceutically acceptable salt of L-carnitine is selected from the group consisting of chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerolphosphate, mucate, magnesium tartrate, 2-amino ethanesulphonate, magnesium 2-amino ethanesulphonate, methanesulphonate, choline tartrate, trichloroacetate, and trifluoroacetate.

4. The method according to claim 1, in which the L-carnitine is administered dissolved in 1000-1500 mL of 5% glucose solution.

5. The method according to claim 1, in which the L-carnitine is administered in parallel to the glucose solution, in a single dose or in divided doses, dissolved in a suitable vehicle such as, for example, distilled water, saline solution, or glucose solution.

6. The method according to claim 1, in which the L-carnitine for oral administration is in the form of tablets, capsules, powders, granules, syrups, elixirs, suspensions or solution.

\* \* \* \* \*